(12) United States Patent
Buntru et al.

(10) Patent No.: US 11,371,047 B2
(45) Date of Patent: Jun. 28, 2022

(54) PROMOTER CONSTRUCT FOR CELL-FREE PROTEIN SYNTHESIS

(71) Applicant: Fraunhofer-Gesellschaft zur Foerderung der angewandten Forschung e.V., Munich (DE)

(72) Inventors: Matthias Buntru, Aachen (DE); Simon Vogel, Aachen (DE); Stefan Schillberg, Aachen (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 251 days.

(21) Appl. No.: 16/480,276

(22) PCT Filed: Jan. 25, 2018

(86) PCT No.: PCT/EP2018/051831
§ 371 (c)(1),
(2) Date: Jul. 23, 2019

(87) PCT Pub. No.: WO2018/138201
PCT Pub. Date: Aug. 2, 2018

(65) Prior Publication Data
US 2019/0376068 A1 Dec. 12, 2019

(30) Foreign Application Priority Data
Jan. 25, 2017 (EP) .................... 17153067

(51) Int. Cl.
*C12N 15/67* (2006.01)
*C12P 21/02* (2006.01)

(52) U.S. Cl.
CPC .............. *C12N 15/67* (2013.01); *C12P 21/02* (2013.01)

(58) Field of Classification Search
None
See application file for complete search history.

(56) References Cited

U.S. PATENT DOCUMENTS

| 6,168,931 B1 | 1/2001 | Swartz et al. |
| 6,337,191 B1 | 1/2002 | Swartz et al. |
| 7,981,617 B2 | 7/2011 | Endo et al. |

FOREIGN PATENT DOCUMENTS

| EP | 1314781 A1 | 5/2003 |
| JP | H1156363 A | 3/1999 |
| WO | 2018/138201 A1 | 8/2018 |

OTHER PUBLICATIONS

PCT/EP2018/051831 International Search Report and Written Opinion dated Apr. 16, 2018.

Chizzolini et al. "Cell-Translation is More Variable than Transcription," ACS Synthetic Biology, Jan. 2017, 6 (4):638-647.
Buntru et al. "Tobacco BY-2 Cell-Free Lysate: An Alternative and Highly Productive Plant-Based in Vitro Translation System," BMC Biotechnology, May 2014, 14(1)37 p. 1-11.
Buntru et al. "A Versatile Coupled Cell-Free Transcription-Translation System Based on Tobacco BY-2 Cell Lysates." Biotechnology and Bioengineering, May 2015, 112(5):867-878.
Chizzolini et al. "Gene Position More Strongly Influences Cell-Free Protein Expression from Operons tham T7 Transcriptional Promoter Strength" ACS Synthetic Biology, Nov. 2013, 3(6):363-371.
End et al. "Zellfreie Proteinexpression Fuer Forschung und Produktion," BioSpektrum, Feb. 2014, 20(1)70-72.
Ikeda et al. "Interactions of the RNA Polymerase of Bacteriophage T7 with its Promoter During Binding and Initiation of Transcription," Proceedings of the National Academy of Sciences USA, Jun. 1986, 83(11):3614-3618.
Stech et al. "A Continuous-Exchange Cell-Free Protein Synthesis System Based on Extracts from Cultured Insect Cells." PLOS One, May 2014, 9(5):e96635.
Bradford, Marion. "A Rapid and Sensitive Method for the Quantitation of Microgram Quantities of Protein Utilizing the Principle of Protein-Dye Binding." Analytical Biochemistry, 1976, 72:248-254.
Carlson et al. "Cell-Free Protein Synthesis: Applications Come of Age." Biotechnology Advances, 2012, 30 (5):1185-1194.
Gait, M.J., "Oligonucleotide Synthesis. A Practical Approach." Aug. 1985, 188(1): 166-167.
Gaille et al. "Identification of the Motifs within the Tobacco Mosaic Virus 5'-Leader Responsible for Enhancing Translation," Nucleic Acids Research, 1992, 20(17):4631-4638.
Goshima et al. "HUman Protein Factory for Converting the Transcriptome into an in Vitro-Expressed Proteome." Nature Methods, Dec. 2008, 5(12)1:1011-1017.
Gursinsky et al. "Replication of Tomato Bushy Stunt Virus RNA in a Plant in Vitro System." Virology, 2009, 390:250-260.
Hoffman et al. "Rapid Translation System: A Novel Cell-Free Way from Gene to Protein." Biotechnology Annual Review, 2004, 10:1-30.
Kovtun et al. "Towards the Construction of Expressed Proteomes Using a Leishmania Tarentolae Based Cell-Free Expression System." Plos One, Dec. 2010, 5(12):e14388:1-11.
Kubick et al. "In Vitro Synthesis of Posttranslationally Modified Membrane Proteins." Current Topics in Membranes, 2009, 63:25-49.
Leader et al. "Protein Therapeutics: A Summary and Pharmacological Classification." Nature Reviews Drug Discovery, Jan. 2008, 7:21-39.
Mignone et al. "Untranslated Regions of mRNAs." Genome Biology, Feb. 28, 2002, 3(3):reviews0004.1-0004.10.

(Continued)

*Primary Examiner* — Kagnew H Gebreyesus
(74) *Attorney, Agent, or Firm* — Wagenknecht IP Law Group PC

(57) ABSTRACT

The technology provided herein relates to novel promoter constructs, method and systems for an increase in the target protein yield and/or allowing the use of lower template concentration in the cell-free protein synthesis systems.

5 Claims, 3 Drawing Sheets
Specification includes a Sequence Listing.

(56) References Cited

OTHER PUBLICATIONS

Mureev et al. Species-Independent Translational Leaders Facilitate Cell-Free Expression, Aug. 2009, Nature Biotechnology, 27(8):747-754.

Sawasaki et al. "A Cell-Free Protein Synthesis System for High-Throughput Proteomics." PNAS, Nov. 12, 2002, 99(23):14652-14657.

Swartz, James R. "Transforming Biochemical Engineering with Cell-Free Biology." American Institute of Chemical Engineers Journal, Jan. 2012, 58(1): 5-13.

Tarui et al. "Establishment and Characterization of Cell-Free Translation/Glycosylation in Insect Cell (*Spodoptera frugiperda* 21) Extract Prepared with High Pressure Treatment." Applied Microbiology and Biotechnology, 2001, 55:446-453.

JP2019560484 Office Action dated Aug. 10, 2021.

SEQ ID NO 3:

FIG. 3

```
            T7 promoter      | tc s | omega 5'UTR|t1 s
V1  TAATACGACTCACTATA-------GTATTT...TACCATG
V2  TAATACGACTCACTATAGAA----GTATTT...TACCATG
V3  TAATACGACTCACTATAGAAGAAGAAGTATTT...TACCATG
V4  TAATACGACTCACTATAGGGAGAGAGTATTT...TACCATG
V5  TAATACGACTCACTATAGGCAGAGAGTATTT...TACCATG
V6  TAATACGACTCACTATAGTAAGAGTATTT...TACCATG
V7  TAATACGACTCACTATAGCAAGAGTATTT...TACCATG
V8  TAATACGACTCACTATAGGAAGAGTATTT...TACCATG
V9  TAATACGACTCACTATAGAAAGAGTATTT...TACCATG
```

PROMOTER CONSTRUCT FOR CELL-FREE PROTEIN SYNTHESIS

CROSS REFERENCE TO RELATED APPLICATIONS

This is a US national phase application under 35 USC § 371 of international patent application no. PCT/EP2018/051831, filed Jan. 25, 2018, which itself claims priority to European application 17153067.8, filed Jan. 25, 2017. Each of the applications referred to in this paragraph are herein incorporated by reference in their entireties.

REFERENCE TO SEQUENCE LISTING SUBMITTED ELECTRONICALLY

The official copy of the sequence listing is submitted electronically via EFS-Web as an ASCII formatted sequence listing with file "PCTEP2018051831_SEQID" created on Jul. 23, 2019 and having a size of 5 Kilobytes. The sequence listing contained in this ASCII formatted document forms part of the specification and is herein incorporated by reference in its entirety.

FIELD OF THE DISCLOSURE

The present technology relates to promoter constructs, method and systems for an increase in the target protein yield and/or allowing the use of lower template concentration in the cell-free protein synthesis systems.

BACKGROUND

The increasing demand for new therapeutic proteins, technical enzymes, protein engineering and functional genomics requires a rapid and efficient protein production and screening platform.

The emerging technology of cell-free protein synthesis (CFPS) can help to satisfy this demand (Carlson et al., 2012). CFPS systems based on crude lysates provide several advantages over in vivo systems and offer broad applications in protein engineering, biopharmaceutical product development and post-genomic research.

Compared to cell-based expression, CFPS offers advantages such as shorter process times and the direct control and monitoring of reaction conditions. PCR products can be used directly for the simultaneous expression of multiple proteins without laborious cloning and transformation steps. CFPS platforms allow the addition of accessory factors that promote protein folding or the incorporation of unnatural amino acids (Albayrak and Swartz, 2013; White et al., 2013). They also facilitate the expression of cytotoxic proteins that cannot be produced in living cells.

Crude lysates contain the necessary components for translation, protein folding, and energy metabolism, so providing them with amino acids, energy substrates, nucleotides and salts allows almost any protein encoded by a RNA template to be synthesized. In coupled transcription/translation systems supplemented additionally with an appropriate RNA polymerase DNA templates can also be used.

As mentioned above, in contrast to traditional cell-based expression methods, CFPS offers shorter process times, limited protein hydrolysis and the ability to express toxic proteins or proteins containing specific chemical groups or unnatural amino acids at defined positions. Furthermore, the open nature of the system allows the reaction to be controlled and monitored directly. Although chemical synthesis allows the rapid and controlled synthesis of peptides <40 residues in length, this is not an economically feasible method for the production of larger polypeptides.

The most widely used cell-free systems are based on *Escherichia coli* extract (ECE), wheat germ extract (WGE), rabbit reticulocytes lysate (RLL) and insect cell extract (ICE). These contain diverse cellular components and cofactors that enhance protein expression, folding and modification in different ways. Therefore, the most appropriate system will depend on the origin and the biochemical nature of the target protein. The preparation of ECE is simple and inexpensive, and generally achieves the highest protein yields, from hundreds of micrograms to milligrams per milliliter in batch reactions depending on the target protein.

In contrast, eukaryotic systems are less productive and extract preparation is more laborious, but complex proteins can be produced more efficiently and extended post-translational modifications are supported. WGE normally yields tens of micrograms to milligrams of recombinant protein per milliliter, depending on the protein and reaction format, but extract preparation takes 4-5 d, and the yield of extract from wheat seeds is low. The yields of RLL systems are typically two orders of magnitude lower than WGE and ICEs prepared from *Spodoptera frugiperda* can achieve yields of up to 50 µg/mL.

Recently two further eukaryotic systems based on CHO cells and *Saccharomyces cerevisiae* have been described. The CHO extract yield up to 50 µg/mL active firefly luciferase, but the fermentation medium is quite expensive. In contrast, the preparation of the yeast extract is inexpensive, but the system produces only low target protein levels of 8 µg/mL active firefly luciferase. The drawbacks of current cell-free systems have therefore created a demand for highly productive eukaryotic cell-free systems that can be prepared quickly in large amounts.

An uncoupled CFPS system based on tobacco BY-2 cells has been described in the literature (Buntru et al. Buntru et al. BMC Biotechnology 2014, 14:37). Furthermore, a highly efficient coupled cell-free transcription-translation system based on tobacco BY-2 cell lysates (BYLs) was also described in the prior art (Buntru et al, Biotechnology and Bioengineering, Vol. 112, No. 5, 2015, 867-878).

Several attempts have been described so far to increase target protein yield in cell-free systems by optimization of the template, e.g. by using different promoters and/or 5' and 3' untranslated regions (UTRs). The omega 5' UTR from Tobacco mosaic virus (TMV) was identified to yield high target protein levels in the cell-free wheat germ extract (WGE) and is also functional in other cell-free translational systems like rabbit reticulocyte lysate (RLL) and *Escherichia coli* extract (ECE) (Gallie et al., 1987; Gallie and Walbot, 1992). Furthermore, Sawasaki et al. (2002) and U.S. Pat. No. 7,981,617 B2 describe the use of a specific triplet (GAA) as transcription start upstream of the omega sequence that increases target protein yield in WGE. However, there is still a need for further improvement of cell-free in vitro protein synthesis.

Therefore, it is an object of the present disclosure to provide methods and constructs for an improved cell-free in vitro protein synthesis.

SUMMARY OF THE DISCLOSURE

The present disclosure relates generally to the field of cell-free protein synthesis (also called in vitro protein synthesis or abbreviated CFPS). More specifically, the present disclosure relates to promoter constructs, method and systems for an increase in the target protein yield and/or allowing the use of lower template concentration in the cell-free protein synthesis systems.

In a first aspect, the present disclosure pertains to novel DNA promoter constructs suitable for an efficient cell-free protein synthesis of a target polypeptide, wherein said DNA promoter construct comprises in the 5'-3' direction:
a) A promoter element of an RNA polymerase,
b) an enhancing element of at least 6 consecutive nucleotides including the transcription start site, wherein the enhancing element comprises the sequence GGGAGA, GCAAGA or GGAAGA,
c) a 5' UTR sequence element, and
d) a translation initiation start site.

The present disclosure pertains in a second aspect to transcription templates for efficiently synthesizing an mRNA for cell-free protein synthesis, wherein the transcription template comprises a promoter construct according to the present disclosure, wherein a polynucleotide and/or gene of interest is linked to the translation initiation start site.

In a third aspect, the present disclosure relates to expression cassettes comprising:
a) A DNA promoter construct according to the present disclosure,
b) a polynucleotide and/or gene of interest linked to said promoter construct, and
c) optionally a transcription end site polyadenylation signal.

In a third aspect, the present disclosure relates to methods for cell-free protein synthesis, said method comprises synthesizing a protein in vitro by using a transcription template according to the present disclosure and/or an expression cassette according to the present disclosure in a cell-free protein synthesis system.

In a fourth aspect, the present disclosure pertains to nucleic acid vectors comprising the promoter construct according to the present disclosure, a transcription template according to the present disclosure or an expression cassette according to the present disclosure.

In a fifth aspect, the present disclosure pertains to cell-free protein synthesis systems suitable for protein synthesis comprising:
a) A prokaryotic or eukaryotic cellular lysate,
b) a reaction buffer, and
c) a transcription template, and/or an expression cassette and/or a nucleic acid vector according to the present disclosure.

Furthermore, the present disclosure pertains to protein screening and/or production platforms comprising a cell-free protein synthesis system according to the present disclosure, and/or a promoter construct, and/or a transcription template, and/or an expression cassette, and/or a nucleic acid vector according to the present disclosure.

BRIEF DESCRIPTION OF THE DRAWINGS

FIG. 3 shows the DNA-sequences of different variants of nucleotides (enhancer element, tc s) as transcription start upstream of the omega 5' untranslated region (UTR). Positions of T7 promoter, transcription start site (tc s), omega 5' UTR and translation start (tl s) are indicated.

DETAILED DESCRIPTION OF THIS DISCLOSURE

Figure 1:
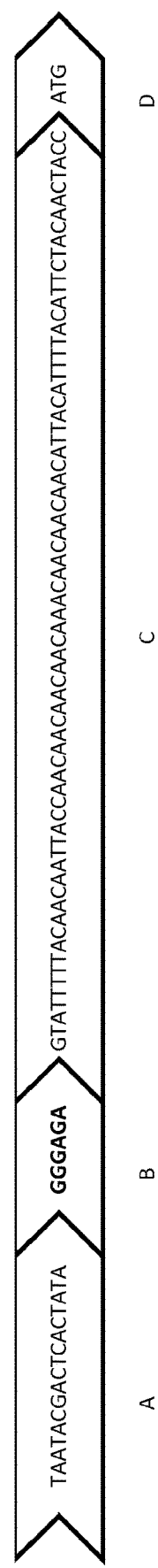
FIG. 1 shows an advantageous embodiment of the DNA promoter construct according to the present disclosure (SEQ ID NO. 3). A: T7 promoter element, B: enhancing element comprising transcription start site, C: omega 5' UTR sequence element, wherein the last 3' nucleotide is changed from A to C (compared to natural omega sequence) to facilitate cloning (integration of gene of interest), D: translation initiation start site.

The present disclosure pertains to novel constructs, methods and systems for cell-free protein synthesis, in particular to cell-free protein synthesis systems suitable for protein synthesis in tobacco BY-2 cell lysate by using a DNA promoter construct comprising a novel enhancer element for increasing the yield of the expressed target protein of interest.

Advantageous embodiments of the present disclosure pertains to DNA promoter constructs suitable for an efficient cell-free protein synthesis of a target polypeptide, wherein said DNA promoter construct comprises in the 5'-3' direction:
a) A promoter element of an RNA polymerase,
b) an enhancing element of at least 6 consecutive nucleotides including the transcription start site, wherein the enhancing element comprises the sequence GGGAGA, GCAAGA or GGAAGA,
c) a 5' UTR sequence element, and
d) a translation initiation start site.

Due to the novel DNA promoter construct, in particular by addition of the enhancer element comprising the extra nucleotides upstream of the 5' UTR element like the omega 5' UTR sequence from TMV in the promoter construct, the expression of a protein of interest could be extremely increased, in particular by using a cell-free BYL system. The original omega sequence without the additional nucleotides of the enhancer element at the transcription start site led to almost no detectable target protein production.

Moreover, the novel DNA promoter constructs, cell-free protein synthesis systems, expression cassettes, methods and transcription templates according to the present disclosure allow the use of very low template concentrations which is an important cost and efficient factor at least in large scale approaches. In small scale screening approaches, e.g. by microfluidic based methods where only minor DNA amounts are present, the novel constructs and systems may increase protein productivity resulting in detectable amounts of the target protein. Most likely the new promoter constructs also lead to increased target protein yield in other cell-free coupled transcription-translation systems than the BYL.

In some advantageous embodiments, the DNA-promoter constructs, the vectors, expression cassettes and/or transcription templates according to the present disclosure are isolated and/or purified. As used herein, the term "isolated" means that the referenced material is removed from its native environment, e.g., a cell. Thus, an isolated biological material can be free of some or all cellular components, i.e., components of the cells in which the native material occurs naturally (e.g., cytoplasmic or membrane component). A material shall be deemed isolated if it is present in a cell extract or supernatant. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined or proximal to non-coding regions (but may be joined to its native regulatory regions or portions thereof), or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like, i.e., when it forms part of a chimeric recombinant nucleic acid construct. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained.

As mentioned above, the DNA promoter constructs according to the present disclosure are suitable for an efficient cell-free protein synthesis. Cell-free protein synthesis (also called in vitro protein synthesis or abbreviated CFPS) is the production of protein using biological machinery without the use of living cells. The in vitro protein synthesis environment is not constrained by a cell wall or homeostasis conditions necessary to maintain cell viability. Thus, CFPS enables direct access and control of the translation environment, which is advantageous for a number of applications including optimization of protein production, optimization of protein complexes, to study protein synthesis, incorporating non-natural amino acids, high-throughput screens, and synthetic biology.

A "promoter element" is a DNA regulatory region capable of binding RNA polymerase in a cell and initiating transcription of a sequence. For purposes of defining the present invention, a promoter sequence which is located upstream of a cDNA is bounded at its 3' terminus by a transcription initiation site and extends upstream (5' direction) to include the minimum number of bases or elements necessary to initiate transcription at levels detectable above background. A promoter sequence which is located downstream of a cDNA (to express a (-)RNA) is bounded at its 5' terminus by a transcription initiation site and extends downstream (3' direction) to include the minimum number of bases or elements necessary to initiate transcription at levels detectable above background.

The DNA promoter construct described herein is preferably the coding strand i.e. the DNA strand whose base sequence corresponds to the base sequence of the RNA transcript produced (although with thymine replaced by uracil). It is this strand that contains codons, while the non-coding strand contains anti-codons. During transcription, RNA polymerase II binds the non-coding strand, reads the anti-codons, and transcribes their sequence to synthesize an RNA transcript with complementary bases. By convention, the coding strand is the strand used when displaying a DNA sequence. It is presented in the 5' to 3' direction.

The present disclosure pertains in particular to novel DNA promoter constructs, wherein the promoter construct comprises a promoter element of an RNA polymerase. A promoter or promoter element is a DNA sequence that directs the transcription of a structural gene. Typically a promoter is located in the 5' region of a gene, proximal to the transcriptional start site of a structural gene (or polynucleotide and/or gene of interest).

The term "RNA polymerase" includes DNA-dependent RNA polymerases (RNA Pol) using specific DNA-sequences or elements to identify and bind the promoter regions in genes to initiate transcription. Certain RNA Pols have only one subunit (e.g., those from bacteriophages like T3 and T7, and mitochondria), while other RNA Pols from bacteria and eukaryotes are multi-subunit enzymes that require additional protein factors for efficient transcription.

The multimeric enzymes are difficult to reconstitute from purified subunits. By contrast, the smaller monomeric RNA Pols from bacteriophages can perform transcription, including termination and release of the transcript from a DNA template, without the aid of additional protein factors. These features make the bacteriophage RNA Pols excellent tools for in vitro transcription reactions.

In some embodiments, the promoter element of an RNA polymerase is a core promoter element, i.e. a minimal promoter or promoter element containing the essential nucleotide sequences for expression of the operably linked coding sequence, including e.g. the TATA box and start of transcription. By this definition, a core promoter may or may not have detectable activity in the absence of specific sequences that may enhance the activity or confer tissue specific activity.

For example the following different phage RNA Pols with distinct DNA sequence specificities are available commercially for in vitro transcription:

```
T7 RNA polymerase
                                          SEQ ID NO. 11
    (Promoter sequence: TAATACGACTCACTATAGGG);

T3 RNA polymerase
                                          SEQ ID NO. 12
    (Promoter sequence: AATTAACCCTCACTAAAGGG);

SP6 RNA polymerase
                                          SEQ ID NO. 13
    (Promoter sequence: AATTTAGGTGACACTATAGAA);
```

The above listed sequence comprises a transcription start site (tc s) at their 3' end (marked in bold letters).

Therefore, in advantageous embodiments the DNA promoter construct of the present disclosure comprises a promoter element of an RNA polymerase, wherein the RNA polymerase is selected from the group of T7 RNA polymerase, T3 RNA polymerase and SP6 RNA polymerase.

In particular, the promoter element of an RNA polymerase is comprised without the original transcription start site. Therefore, the promoter element of an RNA polymerase is for example selected from the group of:

```
Promoter sequence of T7 RNA polymerase
                                        (SEQ ID NO. 6)
    TAATACGACTCACTATA Promoter sequence of T3 RNA polymerase
                                        (SEQ ID NO. 7)
    AATTAACCCTCACTAAA Promoter sequence of SP6 RNA polymerase
                                        (SEQ ID NO. 8)
    AATTTAGGTGACACTATA
```

```
Promoter sequence of K11 RNA polymerase
                                      (SEQ ID NO. 9)
AATTAGGGCACACTATA Promoter sequence of BA14 RNA polymerase
                                      (SEQ ID NO. 10)
TAATACGACTCACTAAT
```

In an advantageous embodiment, the promoter element is derived from the T7 RNA polymerase, in particular the promoter element comprises or consists the sequence of SEQ ID NO. 13.

The DNA promoter construct according to the present disclosure comprises further an enhancing element of at least 6 consecutive nucleotides. Within the enhancing element will be found a transcription initiation site (conveniently defined for example, by mapping with nuclease S1). The transcription start site is the location where transcription starts at the 5'-end of a gene sequence.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix.

A "polynucleotide" or "nucleotide sequence" is a series of nucleotide bases (also called "nucleotides") in DNA and RNA, and means any chain of two or more nucleotides. A nucleotide sequence typically carries genetic information, including the information used by cellular machinery to make proteins.

Said enhancing element is located between the promoter element and the following 5' UTR sequence element e.g. in advantageous embodiments the sequence of the enhancing element starts after the last 3' nucleotide of the promoter element and ends before the first 5' nucleotide of the 5' UTR sequence element. In some further advantageous embodiments, the first nucleotide at the 5' end of said enhancing element between said promoter element and the 5' UTR element is a guanine (G) and the sixth nucleotide at the 3' end of said enhancing element is an adenine (A).

Advantageous embodiments of the enhancing element consist of the sequence GGGAGA, GCAAGA or GGAAGA. In further advantageous embodiments, the enhancing element comprises or consists of the sequence GAAGAA, GTAAGA or GCAAGA.

As mentioned above, the enhancing element is located between the RNA polymerase promoter element and a 5' UTR sequence element. The 5' untranslated region (5' UTR) (also known as a Leader Sequence or Leader RNA) is the region of an mRNA that is directly upstream from the translation initiation codon and the coding sequence, respectively. The 5' UTR sequence element is a DNA-sequence coding the 5' untranslated region on the transcribed mRNA. Within the 5' UTR is a sequence that is recognized by the ribosome that allows the ribosome to bind and initiate translation (reviewed by Mignone et al., 2002). The mechanism of translation initiation differs in prokaryotes and eukaryotes.

In some advantageous embodiments, the 5' UTR sequence element is a DNA sequence coding for the omega 5' UTR sequence from Tobacco mosaic virus (TMV). Other preferred examples for the 5' UTR sequence element are DNA sequences coding for the 5' UTR of the Tobacco etch virus (TEV). An example of the 5' UTR sequence from Tobacco mosaic virus is shown in SEQ ID NO. 14 and from Tobacco etch virus in SEQ ID NO. 15.

Directly after the 5' UTR sequence element the DNA triplet for coding the translation start site is located. The translation start site or start codon is the first codon of a messenger RNA (mRNA) transcript translated by a ribosome. The start codon always codes for methionine in eukaryotes and a modified Met (fMet) in prokaryotes. The most common start codon is AUG.

In some advantageous embodiments the DNA promoter construct suitable for an efficient cell-free protein synthesis of a target polypeptide comprises in the 5'-3' direction:
  a) A T7 promoter element of an RNA polymerase, in particular comprising SEQ ID NO. 12,
  b) an enhancing element of at least 6 consecutive nucleotides including the transcription start site, in particular having the GGGAGA, GCAAGA or GGAAGA,
  c) an omega 5' UTR sequence from Tobacco mosaic virus (TMV), in particular having SEQ ID NO. 14, and
  d) a translation initiation start site.

Therefore, in advantageous embodiments the promoter construct according to the present disclosure comprises a sequence selected from the group consisting of:
  a) A nucleic acid sequence set forth in SEQ ID NO. 3, and
  b) a nucleic acid sequence having at least 85% sequence identity with a).

A further advantageous embodiment of the promoter construct according to the present disclosure comprises a sequence selected from the group consisting of:
  a) A nucleic acid sequence set forth in SEQ ID NO. 4, and
  b) a nucleic acid sequence having at least 85% sequence identity with a).

"Percent sequence identity", with respect to two amino acid or polynucleotide sequences, refers to the percentage of residues that are identical in the two sequences when the sequences are optimally aligned. Thus, 85% amino acid sequence identity means that 85% of the amino acids in two optimally aligned polypeptide sequences are identical. Percent identity can be determined, for example, by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN14, National Biomedical Research Foundation, Washington, D.C., which adapts the local homology algorithm of Smith and Waterman for peptide analysis.15. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters 5 recommended by the manufacturer and described in the Wisconsin Sequence Analysis Package referred to above. An example of an algorithm that is suitable for determining sequence similarity is the BLAST algorithm, which was described before. Software for performing BLAST analyses is publicly available through the National Center for Biotechnology Information (http://www.ncbi.nlm.nih.gov/). Likewise, computer programs for determining percent homology are also readily available.

Furthermore, the present disclosure pertains to transcription templates for efficiently synthesizing an mRNA for cell-free protein synthesis, wherein the transcription template comprises a promoter construct according to the present disclosure, wherein a structural gene, a polynucleotide or a gene of interest is linked to the translation initiation start site.

The transcription templates constructs described in the present disclosure herein are preferably the coding strand i.e. the DNA strand whose base sequence corresponds to the base sequence of the RNA transcript produced (although with thymine replaced by uracil). It is this strand that contains codons, while the non-coding strand contains anti-codons. During transcription, RNA Pol II binds the non-coding strand, reads the anti-codons, and transcribes their sequence to synthesize an RNA transcript with complementary bases. By convention, the coding strand is the strand used when displaying a DNA sequence. It is presented in the 5' to 3' direction.

However, in contrast to the described promoter constructs the transcription template according to the present disclosure comprises a structural gene and/or a polynucleotide and/or gene of interest that is linked to the translation initiation start site.

A structural gene (or polynucleotide and/or gene of interest) is a DNA sequence that is transcribed into messenger RNA (mRNA) that is then translated into a sequence of amino acids characteristic of a specific polypeptide.

Furthermore, the present disclosure relates to expression cassettes comprising:
a) A DNA promoter construct according to the present disclosure,
b) a polynucleotide and/or gene of interest linked to said promoter construct, and
c) optionally a transcription end site polyadenylation signal.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

An "expression cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. Recombinant cloning vectors will often include one or more replication systems for cloning or expression, one or more markers for selection in the host, e.g. antibiotic resistance, and one or more expression cassettes.

The term "synthesis of a target polypeptide" or "expression" refers to biosynthesis of a gene product. In the case of a structural gene, expression/synthesis involves transcription of the structural gene into mRNA and then translation of the mRNA into one or more polypeptides.

The terms "polypeptide", "peptide", or "protein" are used interchangeably herein to designate a linear series of amino acid residues connected one to the other by peptide bonds between the alpha-amino and carboxyl groups of adjacent residues. The amino acid residues are preferably in the natural "L" isomeric form. However, residues in the "D" isomeric form can be substituted for any L-amino acid residue, as long as the desired functional property is retained by the polypeptide. In addition, the amino acids, in addition to the 20 "standard" amino acids, include modified and unusual amino acids.

"Linked" refers to non-covalent or covalent bonding between two or more molecules. Linking may be direct or indirect. Two molecules are indirectly linked when the two molecules are linked via a connecting molecule (linker). Two molecules are directly linked when there is no intervening molecule linking them. As mentioned above, the polynucleotide and/or gene of interest and said promoter construct are linked preferably directly to each other.

A promoter, terminator or polyadenylation signal is "upstream" of a gene if it is proximal to the start of the gene (e.g., the first codon) and distal to the end of the gene (e.g., the termination codon). A promoter, terminator or polyadenylation signal is "downstream" of a gene if it is proximal to the end of the gene and distal to the start of the gene. Promoters in the plasmids of the invention, which are functionally associated with a gene, are oriented so as to promote transcription of a sense or an antisense strand of the gene.

As mentioned above the DNA-promoter construct may e.g. comprise a T7 RNA polymerase promoter, a T3 RNA polymerase promoter or a SP6 RNA polymerase promoter capable of driving expression of a translatable RNA product. For example, the expression cassette optionally may comprise a polyadenylation signal at the 3' end of the transcribed RNA.

The present disclosure pertains also nucleic acid vectors comprising the DNA promoter construct, a transcription template according or an expression cassette according to the present disclosure. The nucleic acid vector may be a cloning vector and/or an expression vector.

The term "vector" includes a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g. bacterial vectors having a bacterial origin of replication and episomal mammalian vectors). Other vectors (e.g. non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression system". In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g. replication-defective retroviruses, adenoviruses and adeno-associated viruses), which serve equivalent functions.

The present disclosure relates also to cell-free protein synthesis systems suitable for protein synthesis comprising:
a) A prokaryotic or eukaryotic cellular lysate,
b) a reaction buffer, and
c) a transcription template, and/or an expression cassette, and/or a nucleic acid vector according to any one of the proceeding claims.

In some advantageous embodiments, the eukaryotic cellular lysate is a tobacco BY-2 cell lysate.

Two basic components are needed to accomplish such in vitro protein expressions: (1) the genetic template (mRNA or DNA) encoding the target protein and (2) a reaction solution containing the necessary transcriptional and translational molecular machinery. Cell extracts (or cell-free protein synthesis (CFPS) system supply all or most of the molecules of the reaction solution, including:
  RNA polymerases for mRNA transcription,
  ribosomes for polypeptide translation,
  tRNAs and amino acids,
  enzymatic cofactors and an energy source,
  cellular components essential for proper protein folding.

Template DNA for cell-free in vitro transcription can be linear, a circular plasmid or a PCR fragment. However, the DNA must contain a promoter sequence upstream of the gene to be transcribed.

Cell lysates provide the correct composition and proportion of enzymes and building blocks required for translation (usually, an energy source and amino acids must also be added to sustain synthesis.) Cell membranes are removed to leave only the cytosolic and organelle components of the cell (hence the term, "cell-free extracts/lysates"). The first types of lysates developed for cell-free protein expression were derived from prokaryotic organisms. More recently, systems based on extracts from insect cells, mammalian cells and human cells have been developed and made commercially available.

The cell-free protein synthesis system according to the present disclosure comprises a biological extract/lysate like a prokaryotic or eukaryotic cellular lysate. The reaction mix for protein transcription/translation will comprise a template for production of the macromolecule, e.g. DNA, mRNA, etc.; monomers for the macromolecule to be synthesized, e.g. amino acids, nucleotides, etc., and such cofactors, enzymes and other reagents that are necessary for the synthesis, e.g. ribosomes, tRNA, polymerases, transcription factors, and an energy regeneration system, e.g. creatine phosphate/creatine kinase, etc. Such synthetic reaction systems are well-known in the art, and have been described in the literature. A number of reaction chemistries for polypeptide synthesis can be used in the methods of the invention. For example, reaction chemistries are described in U.S. Pat. No. 6,337,191, issued Jan. 8, 2002, and U.S. Pat. No. 6,168,931, issued January 2.

Cell-free expression systems can support protein synthesis from DNA templates (transcription and translation) or mRNA templates (translation only). In principle, cell-free expression systems can be designed to accomplish transcription and translation steps as two separate sequential reactions (uncoupled) or concurrently as one reaction (coupled).

Prokaryotic *Escherichia coli* extract based cell-free systems have developed rapidly (for a review, see Carlson, E. D. et al. "Cell-free protein synthesis: Applications come of age," Biotechnol. Adv. 30, 1185-1194, (2012)). For purposes of the invention, any prokaryotic or eukaryotic cellular lysate can be used as a cell-free protein synthesis system. As a prokaryotic cellular lysate as a cell-free protein synthesis system, *E. coli* S30 cell-free extracts were described by Zubay, G. (1973, Ann. Rev. Genet. Vol 7, p. 267). These can be used when the gene to be expressed has been cloned into a vector containing the appropriate prokaryotic regulatory sequences, such as a promoter and ribosome-binding site.

Cell-free systems are considered "coupled" if the transcription and translation occur simultaneously after the addition of DNA to the extract. In some advantageous embodiment, the cell-free protein synthesis system according to the present disclosure is a coupled cell-free protein synthesis system.

However, eukaryotic cell-free lysates are preferred expression systems for many reasons, at least partially because they retain a variety of post-translational processing activities. For example, with the addition of canine microsomal membranes to cell-free wheat germ extract processing events, such as signal peptide cleavage and core glycosylation, can be examined. Eukaryotic cellular lysates also support the translation in vitro of a wide variety of viral and other prokaryotic RNAs, as well as eukaryotic mRNAs.

The major eukaryotic CFPS platforms previously developed include systems made from wheat germ extract (WGE) (Goshima, N. et al. "Human protein factory for converting the transcriptome into an in vitro-expressed proteome," Nat. Methods 5, 1011-1017 (2008); Hoffmann, M. et al. in Biotechnol Annu Rev Vol. 10, 1-30 (Elsevier, 2004); Takai et al. (2010)), rabbit reticulocyte lysate (RRL) (Jackson, R. J. et al. in Methods Enzymol Vol. Vol. 96 (eds. Becca Fleischer, Sidney Fleischer) Ch. 4, 50-74 (Academic Press, 1983)); insect cell extract (ICE) (Ezure, T et al. "A cell-free protein synthesis system from insect cells," Methods Mol. Biol. 607, 31-42 (2010); Kubick, S et al. in Current Topics in Membranes, Vol. 63 (ed. Larry DeLucas) 25-49 (Academic Press, 2009); Tarui, H. et al. "Establishment and characterization of cell-free translation/glycosylation in insect cell (*Spodoptera frugiperda* 21) extract prepared with high pressure treatment," Appl. Microbiol. Biotechnol. 55, 446-453 (2001)); *Leishmania tarentolae* extract (Kovtun, O. et al. "Towards the construction of expressed proteomes using a *Leishmania tarentolae* based cell-free expression system," PLoS One 5, e14388 (2010); Mureev, S. et al. "Species-independent translational leaders facilitate cell-free expression," Nat. Biotechnol. 27, 747-752 (2009)); and HeLa and hybridoma cell extract (Mikami, S. et al. in Cell-Free Protein Production Vol. 607 Methods in Molecular Biology (eds. Yaeta Endo, Kazuyuki Takai, & Takuya Ueda) Ch. 5, 43-52 (Humana Press, 2010)). All these eukaryotic lysates are popular with researchers, and are widely available.

According to the present disclosure, cell extracts used as a cell-free protein synthesis system may be prepared by methods comprising the sequential steps of cell lysis, high-speed centrifugation (30,000 RCF), pre-incubation, dialysis and low-speed centrifugation (4,000 RCF). The cells used in the present disclosure are preferably selected from the group consisting of *E. coli, Bacillus subtilis*, wheat germ, rice germ, barley germ, CHO cells, hybridoma cells and reticulocytes, but not limited thereto.

In an advantageous embodiment of the present disclosure, tobacco BY-2 cell lysates are preferred. This tobacco BY-2 cell lysate could be prepared e.g. by a method described by Buntru et al. BMC Biotechnology 2014, 14:37 and Buntru et al, Biotechnology and Bioengineering, Vol. 112, No. 5, 2015, 867-878 (see examples).

In Table 1, some advantageous embodiments of the enhancing element comprised in the DNA promoter constructs according to the present disclosure are listed (see FIG. 3). Enhancer element V9 is a known enhancer element of the prior art Buntru et al., 2015). In contrast to the enhancer elements known in the prior art, in particular the promoter constructs comprising the enhancer element V4, V5 and V8 surprisingly can be used in very low concentrations which is important for their use in screening assays and/or protein screening and/or production platforms. Therefore, in some advantageous embodiments of the present disclosure, the promoter constructs according to the present disclosure and/or the templates for the protein expression are use in a cell-free protein synthesis system or in methods and/or protein screening and/or production platforms in concentrations between 0.025 and 0.5 µg.

TABLE 1

| Enhancer Element | 5' → 3' |
| --- | --- |
| V3 | GAAGAA |
| V4 | GGGAGA |
| V5 | GGCAGA |
| V6 | GTAAGA |
| V7 | GCAAGA |
| V8 | GGAAGA |
| V9 | GAAAGA |

In Table 2, an advantageous embodiment of the DNA promoter construct according to the present disclosure is shown (SEQ ID NO. 3). SEQ ID NO. 4 is a further embodiment of the promoter construct, SEQ ID NO. 5 is a promoter construct disclosed in the prior art. SEQ ID NO. 1 is the nucleic acid sequence of a promoter construct without an enhancing element between the T7 promoter element and the 5'UTR sequence element, SEQ ID NO. 2 is nucleic acid sequence of a promoter construct having only three nucleic acids between the T7 promoter element and the 5'UTR sequence element. SEQ ID NOs. 6 to 10 are examples for promoter elements of an RNA polymerase without the original transcription start site. SEQ ID NOs. 11 to 13 are examples for promoter elements of an RNA polymerase without the original transcription start site. SEQ ID NO. 14 is an example for an omega 5' UTR sequence from Tobacco mosaic virus (TMV), SEQ ID NO. 15 is an example for an omega 5' UTR sequence from Tobacco etch virus.

TABLE 2

| SEQ ID NO. | 5'→3' |
| --- | --- |
| 1 | TAATACGACTCACTATAGTATTTTTACAACAATTACCAACAACAACAACAAACAACAACAACATTACATTTTACATTCTACAACTACCATG |
| 2 | TAATACGACTCACTATAGAAGTATTTTTACAACAATTACCAACAACAACAACAAACAACAACAACATTACATTTTACATTCTACAACTACCATG |
| 3 | TAATACGACTCACTATAGGGAGAGTATTTTTACAACAATTACCAACAACAACAAACAACAACAACATTACATTTTACATTCTACAACTACCATG |
| 4 | TAATACGACTCACTATAGCAAGAGTATTTTTACAACAATTACCAACAACAACAAACAACAACAACATTACATTTTACATTCTACAACTACCATG |
| 5 | TAATACGACTCACTATAGAAAGAGTATTTTTACAACAATTACCAACAACAACAAACAACAACAACATTACATTTTACATTCTACAACTACCATG |
| 6 | TAATACGACTCACTATA |
| 7 | AATTAACCCTCACTAAA |
| 8 | AATTTAGGTGACACTATA |
| 9 | AATTAGGGCACACTATA |
| 10 | TAATACGACTCACTAAT |
| 11 | TAATACGACTCACTATAGGG |
| 12 | AATTAACCCTCACTAAAGGG |
| 13 | AATTTAGGTGACACTATAGAA |
| 14 | GTATTTTTACAACAATTACCAACAACAACAACAAACAACAACAACATTACATTTTACATTCTACAACTACA |
| 15 | AAATAACAAATCTCAACACAACATATACAAAACAAACGAATCTCAAGCAATCAAGCATTCTACTTCTATTGCAGCAATTTAAATCATTTCTTTTAAAGCAAAAGCAATTTTCTGAAAATTTTCACCATTTACGAACGATAGCA |

As used herein, "expression template" or "nucleic acid template" refer to a nucleic acid that serves as substrate for transcribing at least one RNA that can be translated into a polypeptide or protein. Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template", "nucleic acid template" refer and "transcription template" have the same meaning and are used interchangeably.

As used herein, "translation template" refers to an RNA product of transcription from an expression template that can be used by ribosomes to synthesize polypeptide or protein. The terms "nucleic acid" and "oligonucleotide," as used herein, refer to polydeoxyribonucleotides (containing 2-deoxy-D-ribose), polyribonucleotides (containing D-ribose), and to any other type of polynucleotide that is an N-glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar or phosphate backbone is modified as well as non-purine or non-pyrimidine nucleotide analogs.

In some advantageous embodiments, in the cell-free protein synthesis system and methods according to the present disclosure the protein synthesis is realized in the present of a reaction buffer. The term "reaction buffer" or "reaction mixture" as used herein, refers to a solution containing reagents necessary to carry out a cell-free protein synthesis/expression.

The reaction buffer for promoting cell-free protein synthesis from the DNA transcription template (or RNA translation template) can include additional NTP's and also divalent cation cofactor can be included. A reaction mixture is referred to as complete if it contains all reagents necessary to enable the cell-free protein synthesis.

It will be understood by one of ordinary skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of ordinary skill in the art that reaction components are packaged separately for commercialization and that useful commercial kits may contain any subset of the reaction components of the invention.

A typical set-up for synthesizing a protein in vitro by using said cell-free protein synthesis system is described below. A lysate aliquot is taken from −80° C. storage and thawed at room temperature. To start protein expression, a nucleic acid template is added to the lysate-DNA in case of a coupled transcription-translation reaction and mRNA in case of an uncoupled transcription-translation reaction-plus a reaction mixture composed of HEPES buffer, magnesium glutamate, potassium glutamate, NTP's (ATP, GTP, CTP and UTP for coupled transcription-translation reactions, ATP and GTP for uncoupled transcription-translation reactions), creatine phosphate, creatine kinase, and T7 RNA polymerase (only for coupled transcription-translation reactions) is added. Both coupled and uncoupled transcription-translation reactions are carried out at 25° C. and 700 rpm for 18 h in a thermomixer. Based on the nature of the target protein the synthesized protein can be analyzed by different methods, e.g. fluorescence measurement, enzymatic assay, and SDS PAGE.

EXAMPLES

Preparation of the Tobacco BY-2 Lysate (BYL)

The preparation of lysate from evacuolated BY-2 protoplasts was carried out as described by Komoda et al. (2004) and Gursinsky et al. (2009) with significant modifications. Protoplasts were prepared from cells in the exponential growth phase of a continuous fermentation by treating the cells with 3.5% (v/v) Rohament CL, and 0.2% (v/v) Rohapect UF (both from AB Enzymes, Darmstadt, Germany) directly in the fermentation medium. The osmolarity of the medium was adjusted by addition of 360 mM mannitol. The resulting protoplasts were layered onto a discontinuous Percoll gradient containing (from bottom to top) 70% (v/v, 3 ml), 40% (v/v, 5 ml), 30% (v/v, 3 ml), 15% (v/v, 3 ml) and 0% (3 ml) Percoll (GE Healthcare, Munich, Germany) in 0.7 M mannitol, 20 mM $MgCl_2$, and 5 mM PIPES-KOH (pH 7.0). After centrifugation at 6,800 g for 1 h at 25° C. in a swinging bucket rotor, evacuolated protoplasts were recovered from the 40-70% (v/v) Percoll solution interface. The evacuolated protoplasts were suspended in three volumes of TR buffer (30 mM HEPES-KOH (pH 7.4), 60 mM potassium glutamate, 0.5 mM magnesium glutamate, 2 mM DTT) supplemented with one tablet per 50 ml of Complete EDTA-free Protease Inhibitor Mixture (Roche Diagnostics, Mannheim, Germany) and disrupted using 30 strokes with a Dounce tissue grinder (Sigma-Aldrich, St. Louis, Mo., USA). Nuclei and non-disrupted cells were removed by centrifugation at 500 g for 10 min at 4° C. The supernatant was then frozen in 1 mL aliquots at −80° C.

In Vitro Translation Activity of BYL in Batch Reactions

The performance of the BYL was investigated by producing the reporter protein eYFP using plasmid pIVEX_GAAAGA_Omega_Strep-eYFP as the template. Coupled transcription-translation reactions were performed in 50 µl aliquots at 25° C. and 500 rpm for 16 h in an incubator shaker (Kuehner, Basel, Switzerland). Standard reactions contained 40% (v/v) BYL, 40 mM HEPES-KOH (pH 7.8), 8.5 mM magnesium glutamate, 3 mM ATP, 1.2 mM GTP, 1.2 mM CTP, 1.2 mM UTP, 30 mM creatine phosphate, 0.1 µg/µL creatine kinase, 80 ng/µl vector DNA, and 50 ng/µl homemade T7 RNA polymerase.

The fluorescence signal from eYFP was quantified using a Synergy HT Multi-Mode Microplate Reader (Biotek, Bad Friedrichshall, Germany) with 485/20 nm excitation and 528/20 nm emission filters. The quantity of eYFP was determined by generating a standard curve based on different concentrations of eYFP in BYL transcription-translation reactions without a DNA template. The eYFP standard was produced using the BYL transcription-translation system and purified by Strep-Tactin® Sepharose®. The concentration of purified eYFP was determined using a colorimetric assay (Bradford, 1976).

Template Vector Design and Testing

The transcription start site (tc s) in the vector pIVEX_Omega_Strep-eYFP was modified by addition of different nucleotides upstream of the omega 5' UTR sequence. In total nine different variants were designed and incorporated into the pIVEX_Omega_Strep-eYFP vector in which variant 1 (V1) corresponds to the original sequence without additional nucleotides at the transcription start site and V2 to V9 represent the 8 modified sequences (FIG. 3).

Figure 2:
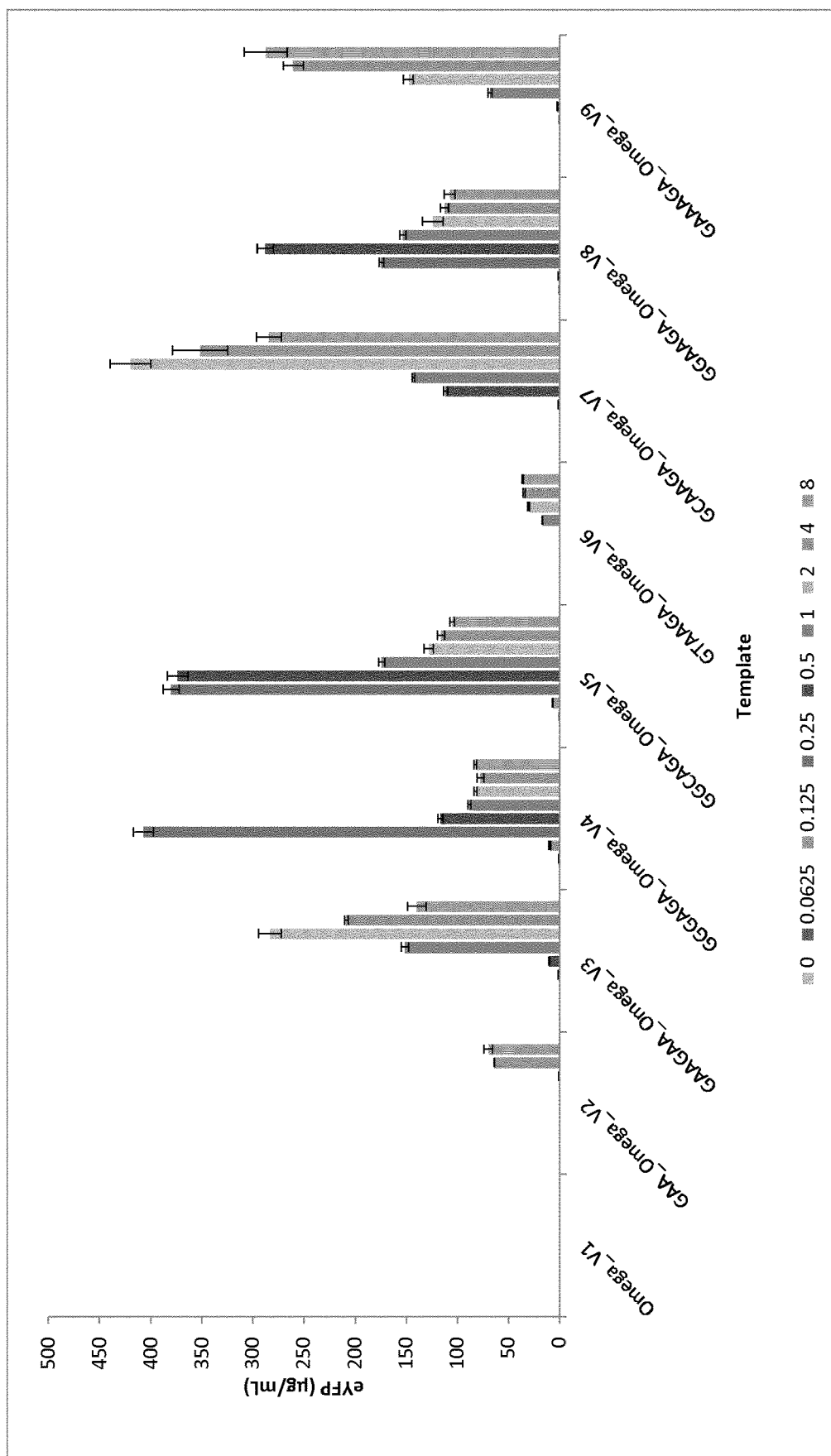
FIG. 2 is a diagram showing the expression of Strep-eYFP using different variants of vector pIVEX_Omega at eight different template concentrations plus the non-vector control. The variants contain different nucleotides (see enhancing elements in FIG. 1 and transcription start site (tc s) in FIG. 3) at the transcription start upstream of the omega 5' untranslated region.

The different vector variants (V1-V9) were compared in coupled transcription-translation system using the cell-free BY-2 lysate (BYL) prepared from tobacco BY2 cells (Buntru et al., 2015). For production of the model protein eYFP containing an N-terminal Strep-tag (Strep-eYFP) eight different template concentrations of 0.0625, 0.0125, 0.025, 0.5, 1, 2, 4, and 8 µg vector (V1-V9) per 50 µl reaction volume were used and each three independent reactions were prepared per sample (FIG. 2). The original omega sequence (V1) without additional nucleotides at the transcription start site led to almost no eYFP accumulation at all template concentrations. The omega sequence with an additional GAA triplet (V2) led to eYFP accumulation only at high template concentration of 4 or 8 µg plasmid per 50 µl reaction. In contrast the variants V4, V5 and V8 resulted in the highest eYFP yields at low template concentrations of 0.25 µg per 50 µl IVTT reaction. The overall highest eYFP yields were achieved using variants V4 and V7. The highest eYFP yield at the lowest template concentrations was achieved using variant V4. As low as 0.0625 µg template plasmid per 50 µl reaction led to a detectable eYFP signal of around 1 µg eYFP per mL lysate.

Results

FIG. 2 shows the expression of Strep-eYFP using different variants of vector pIVEX_Omega at eight different template concentrations (0.0625, 0.0125, 0.025, 0.5, 1, 2, 4, and 8 μg vector (V1-V9) per 50 μl reaction volume). The variants contain different nucleotides at the transcription start upstream of the omega 5' untranslated region. Reactions were performed at 50 μl scale at 25° C. and 500 rpm for 16 h. The fluorescent signal from eYFP was quantified using a fluorescence reader with 485/20 nm excitation and 528/20 nm emission filters. The quantity of eYFP was determined by generating a standard curve based on different concentrations of eYFP in BYL transcription-translation reactions without a DNA template. The eYFP standard was produced using the BYL transcription-translation system and purified by Strep-Tactin® Sepharose®. The concentration of purified eYFP was determined using a colorimetric assay. Data represent the averages and standard deviations of each three independent transcription-translation experiments.

In contrast to the enhancer elements known in the prior art, in particular the promoter constructs comprising the enhancer element V4, V5 and V8 surprisingly can be used in very low concentrations which is important for their use in screening assays and/or protein screening and/or production platforms.

Literature

Bradford M M. 1976. A rapid and sensitive method for the quantitation of microgram quantities of protein utilizing the principle of protein-dye binding. Anal Biochem 72:248-54.

Buntru M, Vogel S, Spiegel H, Schillberg S. 2014. Tobacco BY-2 cell-free lysate: an alternative and highly-productive plant-based in vitro translation system. BMC Biotechnol. 14: 37. doi:10.1186/1472-6750-14-37.

Buntru M, Vogel S, Stoff K, Spiegel H, Schillberg S. 2015. A Versatile Coupled Cell-Free Transcription-Translation System Based on Tobacco BY-2 Cell Lysate. Biotechnol. Bioeng. 112(5):867-78. doi: 10.1002/bit.25502.

Carlson E D, Gan R, Hodgman C E, Jewett M C. 2012. Cell-free protein synthesis: applications come of age. Biotechnol Adv 30(5):1185-94.

Endo Y, Sawasaki T, Ogasawara, T. 2000. Transcription template for cell-free protein synthesis and method using the same. U.S. Pat. No. 7,981,617 B2.

Gallie D R, Walbot V. 1992. Identification of the motifs within the tobacco mosaic virus 5'-leader responsible for enhancing translation. Nucleic Acids Res 20(17):4631-4638.

Gursinsky T, Schulz B, Behrens S E. 2009. Replication of Tomato bushy stunt virus RNA in a plant in vitro system. Virology 390(2):250-60.

Leader B, Baca Q J, Golan D E. 2008. Protein therapeutics: a summary and pharmacological classification. Nat Rev Drug Discov 7(1):21-39.

Mignone F, Gissi C, Liuni S, Pesole G. 2002. Untranslated regions of mRNAs. Genome Biol. 3(3).

Sawasaki T, Ogasawara T, Morishita R, Endo Y. 2002. A cell-free protein synthesis system for high-throughput proteomics. Proc Natl Acad Sci USA 99(23):14652-14657.

Swartz J R. 2012. Transforming Biochemical Engineering with Cell-Free Biology. Aiche Journal 58(1):5-13.

---

What is claimed is:

1. A DNA promoter construct suitable for an efficient cell-free protein synthesis of a target polypeptide, wherein said DNA promoter construct comprises in a 5'-3' direction:
   a) a promoter element of an RNA polymerase;
   b) an enhancing element of at least 6 consecutive nucleotides including the transcription start site, wherein the enhancing element comprises the sequence GGGAGA, GCAAGA or GGAAGA;
   c) a 5' UTR sequence element; and
   d) a translation initiation start site;
   wherein said DNA promoter construct comprises a sequence selected from the group consisting of:
      i) a nucleic acid sequence set forth in SEQ ID NO. 3, and
      ii) a nucleic acid sequence having at least 85% sequence identity with i).

2. A cell-free protein synthesis system suitable for protein synthesis, comprising:
   a) a tobacco BY-2 cell lysate;
   b) a reaction buffer; and
   c) an expression cassette comprising a DNA promoter construct comprising in the 5' to 3' direction:
      i) a promoter element of an RNA polymerase;
      ii) an enhancing element of at least 6 consecutive nucleotides including a transcription start site, wherein the enhancing element comprises the sequence GGGAGA, GCAAGA, or GGAAGA;
      iii) a 5' untranslated region (UTR) sequence element, wherein said 5' UTR sequence element is an omega 5' UTR sequence from Tobacco masaic virus (TMV);
      iv) a translation initiation start site;
      v) a polynucleotide or gene of interest linked to said promoter construct; and optionally,
      vi) a transcription end site polyadenylation signal.

3. The cell-free protein synthesis system according to claim 2, wherein said promoter element of the RNA polymerase is a T7-promoter element.

4. The cell free protein synthesis system according to claim 2, wherein said DNA promoter construct comprises the nucleic acid sequence set forth in SEQ ID NO: 3 or a nucleic acid sequent that has at least 85% sequence identity to SEQ ID NO: 3.

5. A method for cell-free protein synthesis, comprising synthesizing a protein in vitro using the cell-free protein synthesis system according to claim 2.

* * * * *

SEQUENCE LISTING

<160> NUMBER OF SEQ ID NOS: 15

<210> SEQ ID NO 1
<211> LENGTH: 91
<212> TYPE: DNA
<213> ORGANISM: Artificial Sequence
<220> FEATURE:
<223> OTHER INFORMATION: promoter construct without an enhancing element
      between the T7 promoter element and the 5'UTR sequence element

<400> SEQUENCE: 1
taatacgact cactatagta tttttacaac aattaccaac aacaacaaca aacaacaaca      60
acattacatt ttacattcta caactaccat g                                     91

<210> SEQ ID NO 2
<211> LENGTH: 94
<212> TYPE: DNA
<213> ORGANISM: Artificial Sequence
<220> FEATURE:
<223> OTHER INFORMATION: promoter construct having only three nucleic
      acids between the T7 promoter element and the 5'UTR sequence
      element

<400> SEQUENCE: 2
taatacgact cactatagaa gtatttttac aacaattacc aacaacaaca acaaacaaca      60
acaacattac attttacatt ctacaactac catg                                  94

<210> SEQ ID NO 3
<211> LENGTH: 97
<212> TYPE: DNA
<213> ORGANISM: Artificial Sequence

```
<220> FEATURE:
<223> OTHER INFORMATION: DNA promoter construct according to the present
      disclosure

<400> SEQUENCE: 3
taatacgact cactataggg agagtatttt tacaacaatt accaacaaca acaacaaaca      60
acaacaacat tacattttac attctacaac taccatg                              97

<210> SEQ ID NO 4
<211> LENGTH: 97
<212> TYPE: DNA
<213> ORGANISM: Artificial Sequence
<220> FEATURE:
<223> OTHER INFORMATION: DNA promoter construct according to the present
      disclosure

<400> SEQUENCE: 4
taatacgact cactatagca agagtatttt tacaacaatt accaacaaca acaacaaaca     60
acaacaacat tacattttac attctacaac taccatg                              97

<210> SEQ ID NO 5
<211> LENGTH: 97
<212> TYPE: DNA
<213> ORGANISM: Artificial Sequence
<220> FEATURE:
<223> OTHER INFORMATION: Promoter construct prior art

<400> SEQUENCE: 5
taatacgact cactatagaa agagtatttt tacaacaatt accaacaaca acaacaaaca      60
acaacaacat tacattttac attctacaac taccatg                              97

<210> SEQ ID NO 6
<211> LENGTH: 17
<212> TYPE: DNA
<213> ORGANISM: Artificial Sequence
<220> FEATURE:
<223> OTHER INFORMATION: Promoter sequence of T7 RNA polymerase without
      the original transcription start site

<400> SEQUENCE: 6
taatacgact cactata                                                    17

<210> SEQ ID NO 7
<211> LENGTH: 17
<212> TYPE: DNA
<213> ORGANISM: Artificial Sequence
<220> FEATURE:
<223> OTHER INFORMATION: Promoter sequence of T3 RNA polymerase without
      the original transcription start site

<400> SEQUENCE: 7
aattaaccct cactaaa                                                    17

<210> SEQ ID NO 8
<211> LENGTH: 18
<212> TYPE: DNA
<213> ORGANISM: Artificial Sequence
<220> FEATURE:
<223> OTHER INFORMATION: Promoter sequence of SP6 RNA polymerase without
      the original transcription start site

<400> SEQUENCE: 8
aatttaggtg acactata                                                   18
```

```
<210> SEQ ID NO 9
<211> LENGTH: 17
<212> TYPE: DNA
<213> ORGANISM: Artificial Sequence
<220> FEATURE:
<223> OTHER INFORMATION: Promotor sequence of K11 RNA polymerase without
      the original transcription start site

<400> SEQUENCE: 9
aattagggca cactata                                                       17

<210> SEQ ID NO 10
<211> LENGTH: 17
<212> TYPE: DNA
<213> ORGANISM: Artificial Sequence
<220> FEATURE:
<223> OTHER INFORMATION: Promoter sequence of BA14 RNA polymerase
      without the original transcription start site

<400> SEQUENCE: 10
taatacgact cactaat                                                       17

<210> SEQ ID NO 11
<211> LENGTH: 20
<212> TYPE: DNA
<213> ORGANISM: Artificial Sequence
<220> FEATURE:
<223> OTHER INFORMATION: Promoter sequence of T7 RNA polymerase

<400> SEQUENCE: 11
taatacgact cactataggg                                                    20

<210> SEQ ID NO 12
<211> LENGTH: 20
<212> TYPE: DNA
<213> ORGANISM: Artificial Sequence
<220> FEATURE:
<223> OTHER INFORMATION: Promoter sequence of T3 RNA polymerase

<400> SEQUENCE: 12
aattaaccct cactaaaggg                                                    20

<210> SEQ ID NO 13
<211> LENGTH: 21
<212> TYPE: DNA
<213> ORGANISM: Artificial Sequence
<220> FEATURE:
<223> OTHER INFORMATION: Promoter sequence of SP6 RNA polymerase

<400> SEQUENCE: 13
aatttaggtg acactataga a                                                  21

<210> SEQ ID NO 14
<211> LENGTH: 71
<212> TYPE: DNA
<213> ORGANISM: Tobacco mosaic virus

<400> SEQUENCE: 14 gtattttac aacaattacc aacaacaaca acaaacaaca acaacattac attttacatt         60
ctacaactac a                                                             71

<210> SEQ ID NO 15
<211> LENGTH: 143
<212> TYPE: DNA
<213> ORGANISM: Tobacco etch virus
```

```
<400> SEQUENCE: 15
aaataacaaa tctcaacaca acatatacaa aacaaacgaa tctcaagcaa tcaagcattc      60
tacttctatt gcagcaattt aaatcatttc ttttaaagca aaagcaattt tctgaaaatt     120
ttcaccattt acgaacgata gca                                            143
```